(12) United States Patent
Milburn

(10) Patent No.: US 11,497,949 B2
(45) Date of Patent: Nov. 15, 2022

(54) ANIMAL HARNESS AND LEASH SYSTEM

(71) Applicant: Lisa Milburn, Overland Park, KS (US)

(72) Inventor: Lisa Milburn, Overland Park, KS (US)

(*) Notice: Subject to any disclaimer, the term of this patent is extended or adjusted under 35 U.S.C. 154(b) by 96 days.

(21) Appl. No.: 16/827,370

(22) Filed: Mar. 23, 2020

(65) Prior Publication Data

US 2020/0298034 A1    Sep. 24, 2020

Related U.S. Application Data

(60) Provisional application No. 62/821,954, filed on Mar. 21, 2019.

(51) Int. Cl.
| | | |
|---|---|---|
| *A01K 27/00* | (2006.01) | |
| *A41D 13/00* | (2006.01) | |
| *A62B 35/00* | (2006.01) | |
| *A61B 5/0205* | (2006.01) | |

(52) U.S. Cl.
CPC ........ *A62B 35/0037* (2013.01); *A01K 27/003* (2013.01); *A01K 27/008* (2013.01); *A41D 13/0007* (2013.01); *A61B 5/0205* (2013.01)

(58) Field of Classification Search
CPC .... A01K 27/002; A01K 27/00; A01K 27/005; A01K 27/0011; A01K 27/003; A01K 27/004; A01K 27/008; A47D 13/086; A41D 13/0007; A61B 5/02438; A61B 5/6831; A61B 5/6805
See application file for complete search history.

(56) References Cited

U.S. PATENT DOCUMENTS

| | | | | |
|---|---|---|---|---|
| 3,004,519 | A * | 10/1961 | Weissman | A47D 15/006 119/857 |
| 5,692,456 | A * | 12/1997 | Louks-Phillips | A62B 35/0006 119/770 |
| 5,988,315 | A * | 11/1999 | Crane | A45F 5/00 182/3 |
| 6,035,440 | A * | 3/2000 | Woodyard | A41D 13/0007 182/3 |
| 6,378,465 | B1 * | 4/2002 | Austin | A62B 35/04 119/770 |
| 7,467,604 | B1 * | 12/2008 | Werner | A01K 27/00 119/770 |

(Continued)

OTHER PUBLICATIONS

"The New Revolutionary Hands-Free Dog Control Harness", Hands Free Dog Harness, accessed at: https://www.handsfreedogharness.com/ on Jun. 23, 2020, 3 pgs.

*Primary Examiner* — Kristen C Hayes
(74) *Attorney, Agent, or Firm* — Husch Blackwell LLP

(57) ABSTRACT

A system and method for providing hands-free animal walking. The system generally comprises a human support device and an animal leash system. The human support device further includes a back center strap, at least one shoulder strap, and an adjustable body strap, to provide ergonomic support and even distribution of force to the user. The animal leash system further includes an elastic leash system to connect the human support device to an animal. When combined, the animal harness and leash system provides an improved, ergonomically sound hands-free animal walking system. The system is particularly adapted for hand-held health sensors, to track health information of the user.

7 Claims, 6 Drawing Sheets

(56) References Cited

U.S. PATENT DOCUMENTS

| | | | |
|---|---|---|---|
| 8,413,613 B1* | 4/2013 | Smith | A01K 27/003 |
| | | | 119/797 |
| 8,534,233 B1* | 9/2013 | Han | A01K 27/003 |
| | | | 119/795 |
| 8,776,266 B1* | 7/2014 | Metz | A41D 13/0007 |
| | | | 2/94 |
| 2009/0044763 A1* | 2/2009 | Russo | A01K 27/003 |
| | | | 119/770 |
| 2013/0047312 A1* | 2/2013 | Wilson | A45F 5/02 |
| | | | 2/69 |
| 2015/0053734 A1* | 2/2015 | Smith | A01K 27/005 |
| | | | 224/576 |
| 2015/0099251 A1* | 4/2015 | Anderson | A01K 27/002 |
| | | | 434/253 |
| 2021/0169417 A1* | 6/2021 | Burton | A61B 5/02055 |

* cited by examiner

ANIMAL HARNESS AND LEASH SYSTEM

CROSS-REFERENCE TO RELATED APPLICATIONS

This Application claims priority to U.S. Provisional Patent Application Ser. No. 62/821,954, filed on Mar. 21, 2019, to Lisa Milburn, entitled "Animal Harness and Leash System," the entire disclosure of which is incorporated herein by reference.

FIELD OF THE INVENTION

The present invention relates to a system and method for walking an animal using a harness and leash system that allows for an improved dog walking experience that is hands free and is also ergonomically engineered.

BACKGROUND OF THE INVENTION

Presently, there is only antiquated equipment and methods for walking animals, primarily for dogs, but particularly there are limited safe hands-free systems to improve this animal walking experience. Further, these limited systems and methods presently designed do little to improve the human experience. Even further, the current equipment used in animal walking does little to prevent health issues for humans and animals, and in some cases, can even increase the chance for health risks.

Currently, the most common animal leash systems consist of a singular hand-held leash. This system is flawed in several aspects. The hand-held leash system relies on the user being able to physically restrain the animal they are walking by holding onto the leash by hand. Further, when the animal pulls away from the user, force is applied to the arm and can forcibly jerk the user's arm and shoulder. This can cause significant pain and discomfort to the user's arm and shoulder, and even to the back and spine. The hand-held leash system may also pose risk to the public. If the user is not paying close attention, or if the animal suddenly pulls away from the user, the animal can break free and create health and safety risks to third parties. These health and safety problems are only increased in the elderly, the physically challenged, and users with health ailments.

While hand-held leash systems are the most popular animal walking systems, there are presently hands-free options for animal walking available. The present hands-free systems utilize a belt or similar apparatus that wraps around the waist of the user, or shoulder straps located solely around the shoulders, and a leash that connects the belt to the animal. However, the current systems are not without flaws. These systems are limited in storage capabilities. Any pockets or other storage components are limited in size to the size of the belt. Additionally, the belt system does not address the ergonomic and health issues of animal walking. Even further, the current systems do not provide support for the user's back, shoulders, or necks. If the animal pulls against the user, then force is applied directly to the lower back of the user, which can cause pain and long-term health problems. Additionally, force applied to the lower back or waist could cause balance issues to the user.

In addition to antiquated and ergonomically challenged animal walking systems, there are limited, to no, systems or methods that motivate individuals and groups, which can also capture social opportunity, improve health and well-being, and animal-to-owner connection. Currently, animal walking is an independent activity and quickly become a chore. Therefore, there is a need for improved social connections and community involvement that are lacking in today's society that can be integrated with animal walking systems. Even further, there is a need for meaningful health tracking that can capture real time metrics that can be provided to medical professionals.

SUMMARY OF THE INVENTION

The present invention comprises an ergonomically designed, human support device and an animal leash system. The human support device includes a back center support strap, at least one shoulder strap, and an adjustable body strap, which provides an even distribution of force, and ergonomic structural support to the user. The human support device can further include at least one sternum strap, for improved fit and comfort. The human support device may further include a vest, that can partially surround the human support device. The vest may include at least one pocket for storage.

The present invention further comprises an animal leash system. The animal leash system can be used to attach the human support device to an animal, for a hands-free animal walking system. The animal leash system can comprise an upper and lower leash, connected together through use of a connection point, such as a proprietary ring. The upper and/or lower leash may be made from elastic material, to allow for additional force distribution when walking an animal.

Because of the hands-free nature of the present invention, handheld digital sensors may further be connected to the system, to allow for the capture of health information. Such information may include pulse, blood pressure, temperature, and the like. The information collected by the digital sensors may be uploaded to doctors or other medical professionals, to provide real-time health metrics.

Other and further objects of the invention, together with the features of novelty appurtenant thereto, will appear in the course of the following description.

DESCRIPTION OF THE SEVERAL VIEWS OF THE DRAWING

In the accompanying drawing, which forms a part of the specification and is to be read in conjunction therewith in which like reference numerals are used to indicate like or similar parts in the various views.

DETAILED DESCRIPTION OF THE INVENTION

Figure 1:
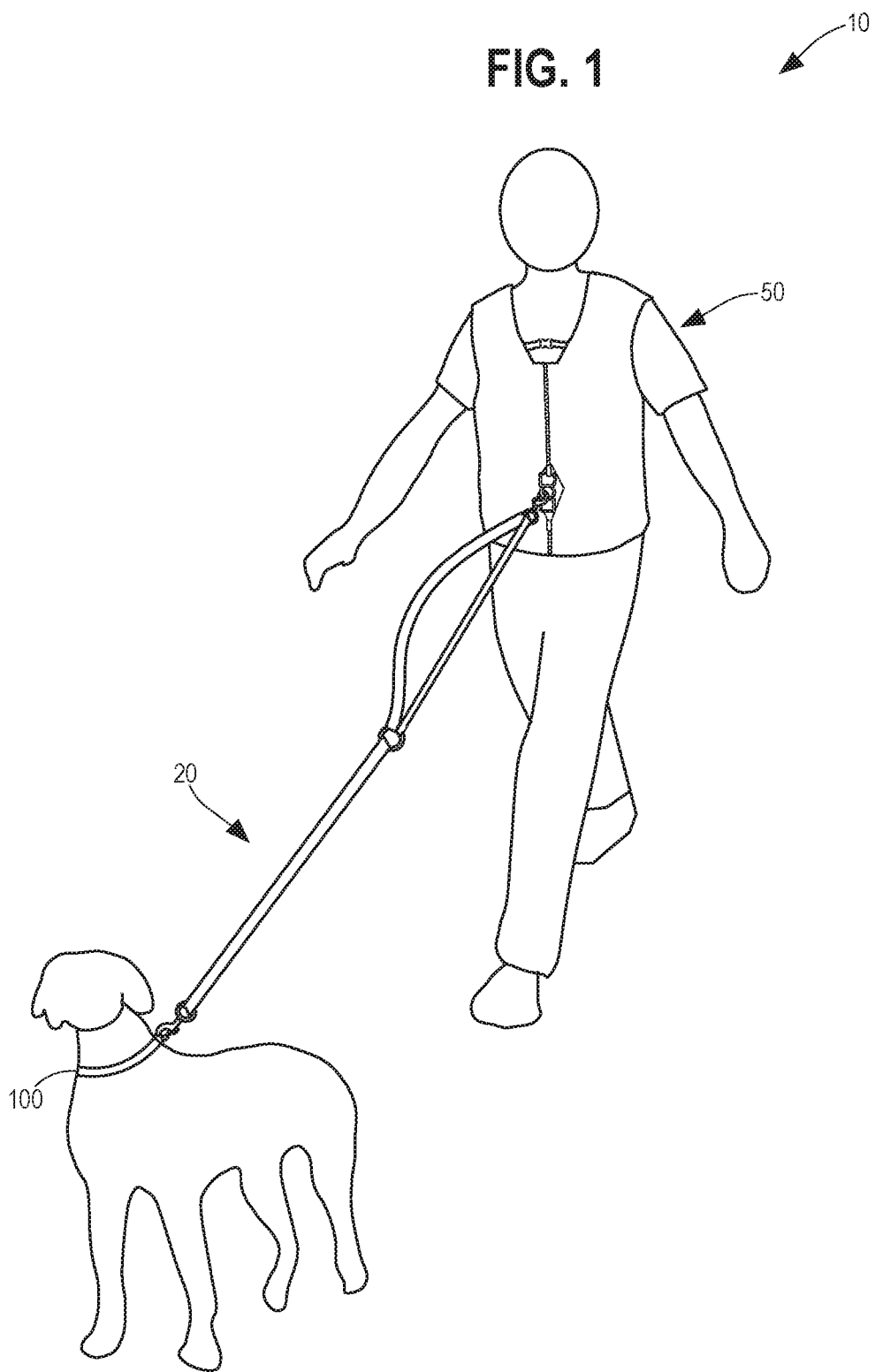
FIG. 1 is a front perspective view of an animal harness and leash system as used with a single animal in accordance with one embodiment of the present invention.

The invention will now be described with reference to the drawing figures, in which like reference numerals refer to like parts throughout. For purposes of clarity in illustrating the characteristics of the present invention, proportional relationships of the elements have not necessarily been maintained in the drawing figures.

The following detailed description of the invention references specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The present invention is defined by the appended claims and the description is, therefore, not to be taken in a limiting sense and shall not limit the scope of equivalents to which such claims are entitled.

The present invention is directed to an ergonomically-designed, animal walking system to improve the animal walking experience into a more enjoyable social opportunity and improve the health benefits of animal walking, for both the user and the animal. The present invention improves the animal-to-human connection, the animal-to-human relationship, animal health and safety, human health and safety, and improves human awareness while walking an animal. This system advances the long needed human health factor in animal walking. The present invention also transforms the traditional animal walking experience to a more social experience, building community and neighborhood relationships. By improving the community relationship, not only is the individual animal owner benefiting, but the community as a whole will improve. The system further aids in forming relationships for alternate and substitute volunteer dog walkers and caregivers. The present invention also provides opportunities for individuals who were previously unable to comfortably walk an animal to finally join in the experience in a comfortable, enjoyable, and safe way, by providing a hands-free, ergonomically sound animal walking system. Even further, the system provides intentional, and meaningful health and medical data collection, in that it may be combined with external medical devices to track and monitor the user's vitals and health information. The health benefits and value of the present invention can be amplified through partnerships with healthcare providers, by providing real time, or logged, accurate health information. The present invention removes the social stigmas of postural braces by providing an aesthetically pleasing design, and can even help remove the social stigma of using postural braces.

In addition to the ergonomic, health, and social advantages, the system also provides an all-in-one kit to organize and integrate animal walking equipment and gear such as phones, keys, drinks, and animal waste collection. The system is further designed for hands-free animal handling as well as a hands-free walking experience. Even further, the system contains various pockets for storage of keys, phones, water, and other items, allowing the user an easy and safe place to store valuables while walking their animal.

Further, the present invention may also improve control and training of animals. Unlike other hands-free animal walking systems that fit only around the waist or shoulders of the user, the present system is positioned around the entire torso, providing greater distribution of force. This distribution of force allows the user to keep their balance and positioning even when the animal is trying to pull away, providing balance and allowing for greater control over the animal. In traditional animal leash systems, a pulling animal generates force to one point, either against the arm of the user in a hand-held leash or against one point on the waist. This increases the chances of the animal breaking free from the users grasp, or causing balance issues for the user. Even further, the safe, hands-free feature of the present system provides opportunity for animal training through a highly responsive combination of hand gestures and gazing that signals intent-to-communicate, which is unavailable in many of the present systems and technology. The hands-free nature of the system, as well as the postural support, improves body language signals for enhanced control and command over the animal.

Figure 2:
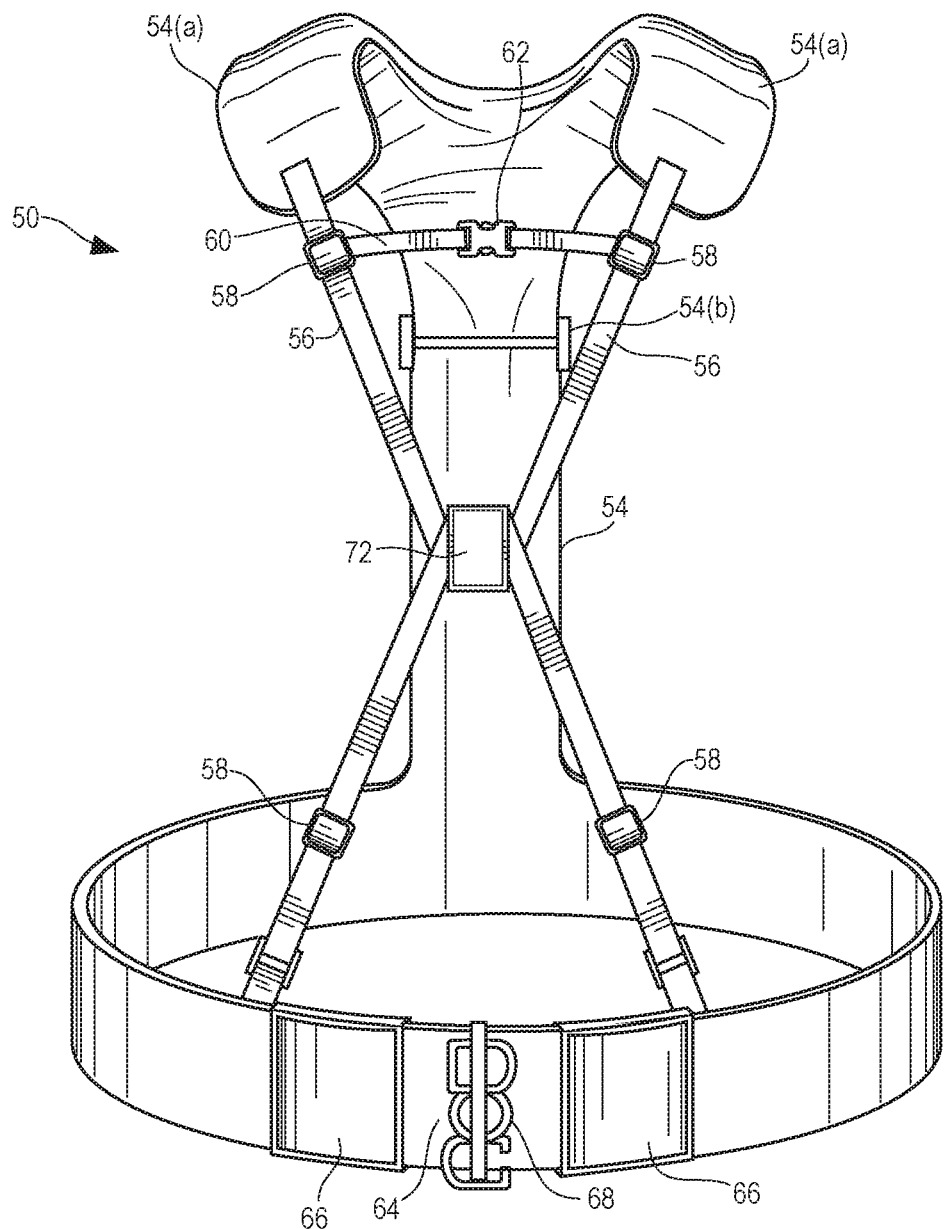
FIG. 2 is a front perspective view of a human support device of the animal harness and leash system of FIG. 1.
Figure 3:
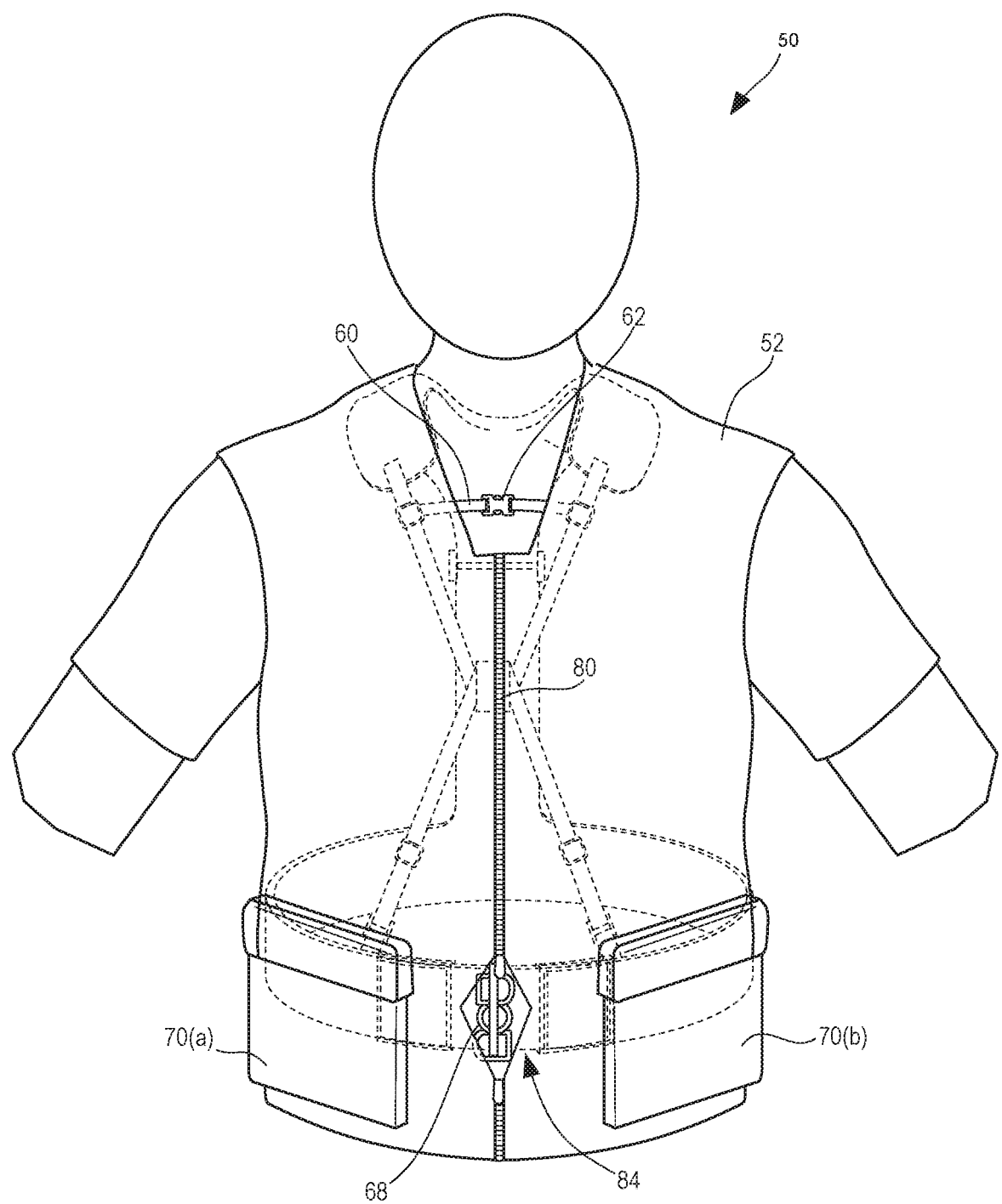
FIG. 3 is a front perspective view of a vest encasing the human support device of FIG. 1.
Figure 4:
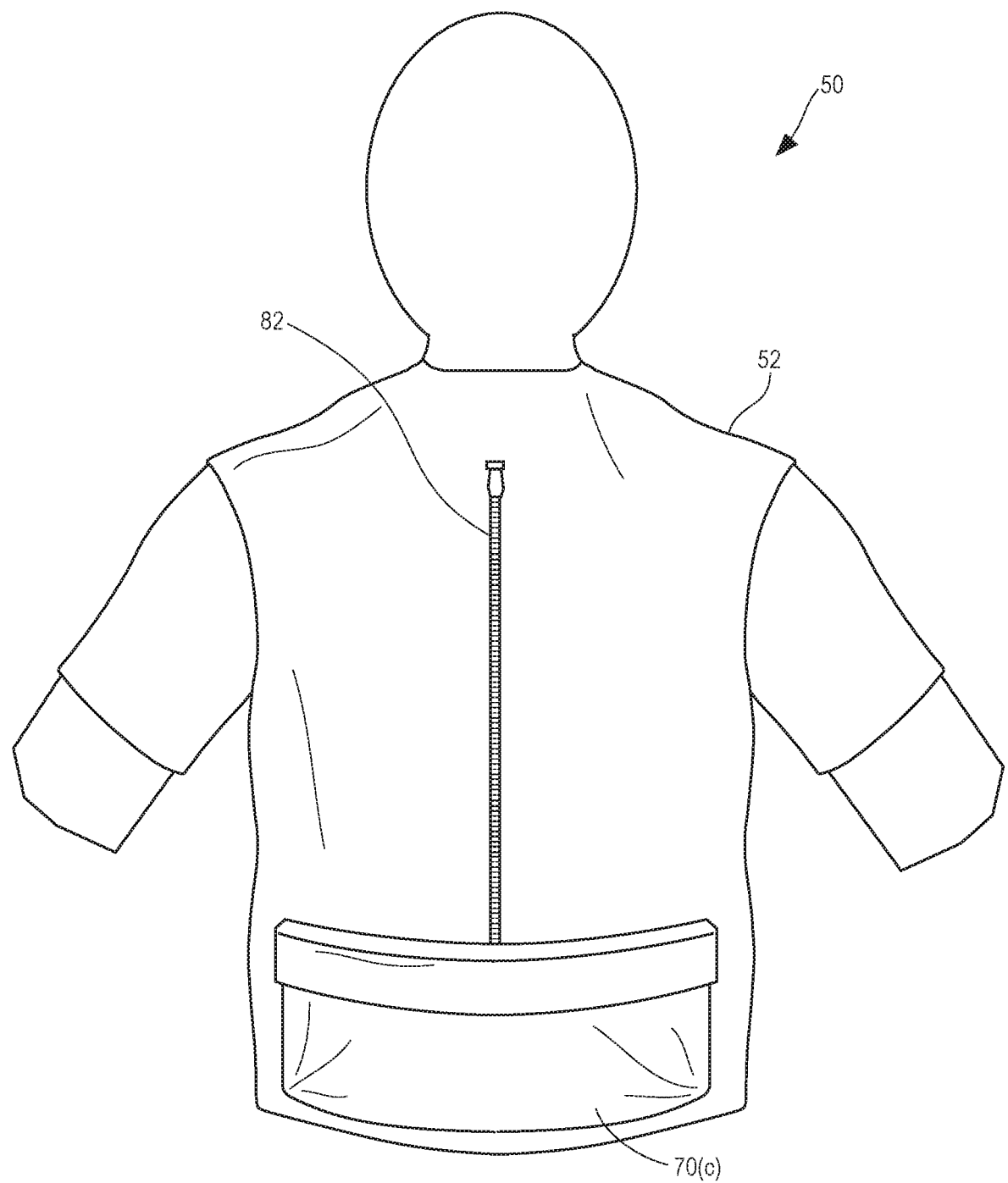
FIG. 4 is a rear perspective view of the vest of FIG. 3.
Figure 6:
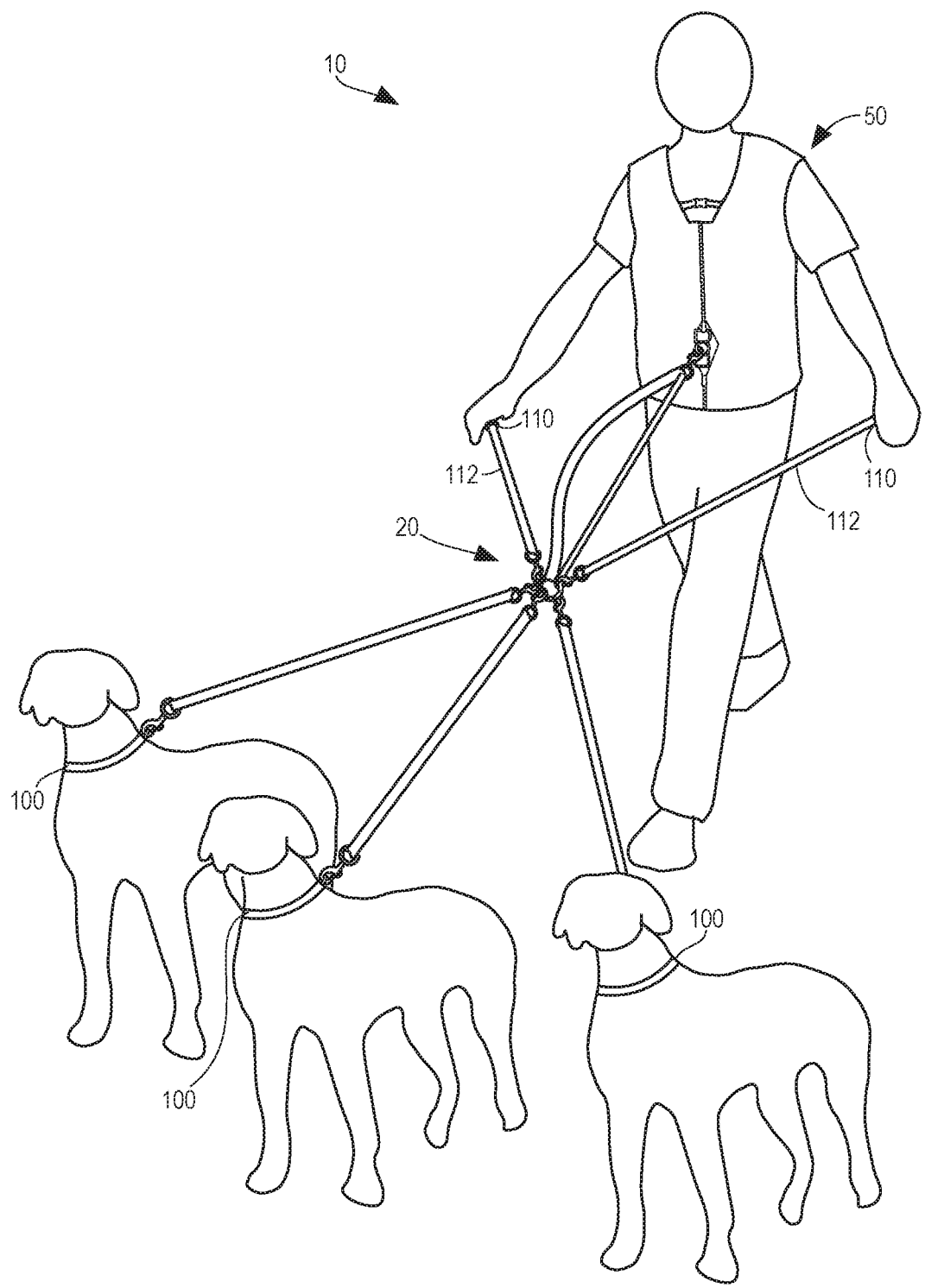
FIG. 6 is a front perspective view of the animal harness and leash system with a plurality of graspable handles as used with multiple animals in accordance with one embodiment of the present invention.

The present invention is generally directed to an animal harness and leash system 10, as shown in FIGS. 1 and 6. The system 10 includes a human support device 50 and an animal leash system 20. The human support device 50 as shown in FIGS. 2-4 is designed as an upper body postural support system with multiple points of stability, combined with a connected hardware for the leash system 20 for connection to the animal, or can be used as a standalone postural support system for sports activity, and even upper body postural training. The system 10 is not limited in scope as to what animals it can be applied to, and it will be appreciated by a person skilled in the art that the system can be used on a variety of animals including, but not limited to dogs, cats, pigs, and other animals.

As shown in FIGS. 2-4, the human support device 50 comprises: (a) a vest 52; (b) a back center support strap 54; (c) at least one shoulder strap 56; (d) at least one shoulder strap fastener(s) 58; (e) a sternum strap 60; (f) at least one sternum strap fastener(s) 62; (g) a body strap (belt) 64; (h) at least one body strap adjuster 66; and (i) a primary ring 68, or similar hardware, attached at the hardware 64 to receive the leash system 20 (as shown in FIGS. 1 and 6) or graspable handles 110 (as shown in FIG. 6). It will also be appreciated that the human support device 50 can further comprise at least one adjuster(s) 54(b) located on the back center strap 54, or similar articles, at horizontal increments to adjust for body height, which can be attached with reinforced stitching and placket.

The human support device 50 may be made out of expandable fabric than can adjust the apparel size. It will be appreciated that human support device 50 may be made out of a variety of material, including, but not limited to, cotton, wool, expandable fabric, micro wick material, and other materials. The human support device 50 may be adjustable to fit a plurality of different sizes and may use snaps, ties, zips on fabric, or any other appropriate method to achieve such tailoring. Further, the human support device 50 may also be made in a plurality of different styles, including, but not limited to, cargo style apparel, mesh, fitted sport apparel, or other styles.

As illustrated in FIG. 2, in one embodiment of the human support device 50, a back center support strap 54 may be incorporated. The back center support strap 54 aligns with the user's back, providing ergonomic support and comfort. Back center support strap 54 may further comprise at least one adjuster 54(b), allowing the length of the back center support strap 54 to be adjusted, to fit users of varying heights. The back center support strap 54 may further comprise at least one shoulder pad 54(a) so that when the user puts on the human support device 50, the at least one shoulder pad 54(a) wraps over the users shoulders, and provides additional support as well as comfort to the user. As shown in FIG. 2, the human support device 50 can comprise two shoulder pads 54(a), providing comfort and support to both shoulders. The human support device 50 can also comprise a body strap or belt 64 that fits above the hip or waist and below the ribs of the user. The belt 64 may then be attached to the back center support strap 54 through mechanical, tailored, or other means. Belt 64 may further contain a fastening apparatus (not shown) allowing the belt 64 to lock or fasten in place at the front, or it may be a single unit that can be adjusted in length, and slipped on the user. Belt 64 can further be adjusted in length to accommodate the size of the user. Belt 64 may be adjustable using one or more body strap adjuster(s) 66, incorporated into the belt 64. The body strap adjuster(s) 66 may utilize buckles, straps, or other methods of adjustment, allowing belt 64 to adjust in size to tailor for the specific needs of the individual user.

As illustrated in FIG. 2, the human support device 50 may further comprise at least one shoulder strap 56 extending from the back center support strap 54, and may be connected or attached at the at least one shoulder pads 54(*a*). The at least one shoulder strap(s) 56 may then extend around the front of the user, and can attach at the belt 64. The at least one shoulder strap(s) 56 may be affixed to the belt using a variety of fastening methods including, but not limited to a bolt, clamp, hook, latch, or other fastening methods. As illustrated in the FIG. 2, the human support device 50 may comprise two shoulder straps 56, coupled together at the center of the torso, using a buckle 72, or other fastening method, mechanically locking the shoulder straps in place. The at least one shoulder strap(s) 56 may be constructed from a flexible or elastic material, such that the at least one shoulder strap(s) 56 may vary in length to ease in achieving positioning. The length and tightness of the at least one shoulder strap(s) 56 can be adjustable and can be adjusted at the at least one shoulder strap fastener 58. As illustrated in FIG. 2, the human support device 50 may further comprise a singular or plurality of shoulder strap fastener(s) 58 at multiple points to provide several points of adjustment. The shoulder strap fastener(s) 58 may be a buckle, or similar adjustable fastener. The primary ring 68 can attach to the front of the belt 64 as a receiving point for the leash system 20 as described herein.

Even further provided but not specifically shown in the figures, the human support device 50 may further comprise the at least one sternum strap 60 for additional support and adjustment, allowing the human support device 50 to fit around, or otherwise encompass the user. The sternum strap 60 may be located in the upper region of the human support device 50, generally around the chest of the user. The sternum strap 60 may be connected to each of the at least one shoulder straps 56, thereby connecting two shoulder straps 56 together. As illustrated in FIG. 2, the sternum strap 60 may comprise two halves, connected at a sternum strap buckle 62. The sternum strap buckle 62, may additionally be used to adjust the length of the sternum strap 60 allowing for varying sizes of users. It will be appreciated that the sternum strap buckle 62 could also be a hook, button, or other fastening system, depending on the embodiment of the human support device 50.

As illustrated in FIG. 2, by fitting around, or encompassing the user's torso, the human support device 50 provides structural support to the user's back, keeping the back straight and applying constant and even pressure throughout the entire torso, rather than at a singular point. This distribution of force relieves pressure to the user and allows the user to walk longer and more comfortably.

As further illustrated in FIGS. 3-4, the human support device 50 may further comprise the vest 52, jacket, or similar apparatus that can at least partially cover the human support device 50. The vest 52 may be sleeveless, short sleeved, or long sleeved, depending on the embodiment of the system 10, and the preference of the user. The vest 52 may be designed with an open front that can open and close using a zipper fastening system 80. As illustrated in FIG. 4, zipper fastening system 80 may additionally be located on the back of the vest 82, and it will be appreciated that there may be two zipper fastening systems, located on the front and the back of the vest 52. It will be appreciated that the vest 52 can utilize a plurality of fastening methods including, but not limited to, a notch, buttonhole, or other fastening methods. As illustrated in FIG. 3, the zipper fastening system 80 may leave an opening 84 or otherwise allow access to the primary ring 68, for attaching the animal leash system 20 to the human support devise 50. The vest 52 may be a separate component of the system 10, or it may be affixed directly to the human support device 50. The vest 52 may be tailored, adhered, or otherwise connected to the human support device 50, such that they are permanently connected. It will be appreciated that in alternative embodiments, the vest 52 may be temporarily attached to the human support device 50, such that it can be removable, and placed on and off, depending on the choice of the user.

As illustrated in FIGS. 3-4, the vest 52 may also feature at least one pocket 70(*a*), (*b*), and/or (*c*) on the exterior of the vest 52 for storage. The least one pocket 70(*a*), (*b*), and/or (*c*) may vary in size to fit numerous embodiments. As depicted in FIGS. 3-4, the vest 52 may comprise three pockets: a rectangular pocket located on the front of the vest to the right of the zipper 70(*a*), a rectangular pocket located on the front of the vest, to the left of the zipper 70(*b*), and a rectangular pocket located at the back of the vest 70(*c*). It will be appreciated that the pocket(s) can vary in number, size, shape, and location based on the embodiment of the invention. It will be further appreciated that the least one pocket 70(*a*), (*b*), and/or (*c*) may be located on the human support device 50, on the vest 52, or both. For example, at least one pocket 70(*a*), (*b*), and/or (*c*) could attached to belt 64 of the human support device 50, in an embodiment that does not comprise the vest 52. The least one pocket 70(*a*), (*b*), and/or (*c*) may comprise a carbon filter liner suitable for pet waste in pet waste bag. It will be appreciated that the least one pocket 70(*a*), (*b*), and/or (*c*) may be made out of numerous materials including carbon lining, cotton, wool, and other textile materials. It will be further appreciated that in an embodiment with a plurality of pockets that not all pockets will be made with the same textile material. The at least one pocket 70(*a*), (*b*), and/or (*c*) may be designed to be compatible with a variety of items including, but not limited to, phones, keys, water reservoirs, or a variety of other items. The at least one pocket 70(*a*), (*b*), and/or (*c*) may also contain an interior hook, tab, or other fastener to secure phones, keys, water reservoirs, or other items. In this embodiment, the user can walk their animal hands-free by placing items normally held in their hands, inside the least one pocket 70(*a*), (*b*), and/or (*c*).

The system 10 may further be fitted to incorporate logos and symbols (not shown) for branding and trademark identification purposes, and depending on the embodiment of the present invention, branding, logos, an/or symbols may be placed on the vest 52, pocket(s) 70(*a*), (*b*), and/or (*c*), straps 56, or leash system 20, or at various other points on the system 10. The vest 52 may further include reflective material, to provide an additional safety feature to the system 10. The vest 52 may achieve this through use of brightly colored fabric of the vest 52 itself, illuminated attachments, or reflective attachments. It will be further appreciated that the vest 52 may further comprise additional safety features, which are within the scope of the invention.

Figure 5:
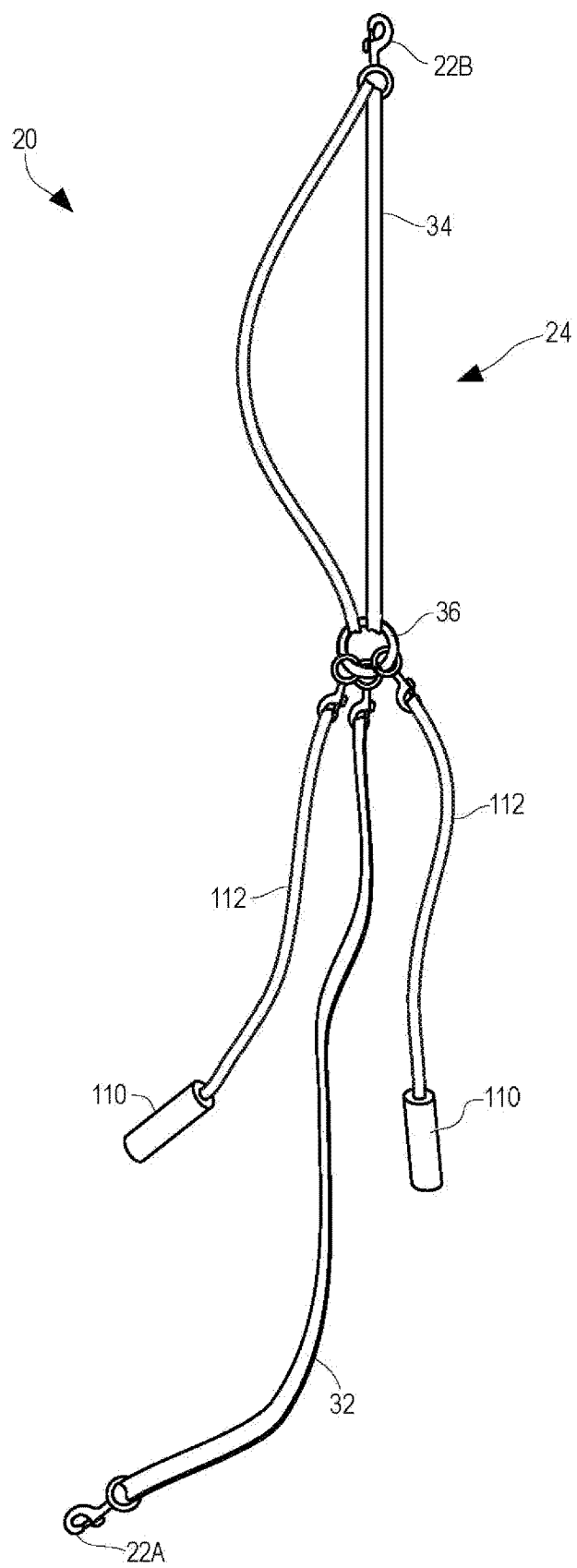
FIG. 5 is a front perspective view of a leash system of the animal harness and leash system of FIG. 1.

As shown in FIGS. 1, 5, and 6, the system 10 also comprises the leash system 20, coupled to the human support device 50, thereby connecting the animal to the human. Leash system 20 may comprise a leash 24 with a safety hook 22A-B at each end of the leash 24. It will be appreciated that safety hooks 22A-B may be replaced with a different fastening method depending on the embodiment of the system 10. Further, it will be appreciated that leash 24 may vary in length depending on the embodiment, to suit the needs of the walker and the animal being walked. Additionally, leash 24 may be fixed in length, or it can be adjustable in length, using any of the commonly known methods of adjusting a leash. In the present embodiment, one of the safety hooks 22A may be affixed to primary ring 68 located at the front of belt 64. Safety hook 22B located at the far-end of the leash 24 may attach to an animal harness or collar 100. It will be appreciated that a traditional loop handle or graspable handle may be attached to primary ring 68 located on belt 64. Leash 24 may comprise an upper leash 32 and a lower leash 34 connected by a secondary ring 36 or similar connecting device. As illustrated in FIG. 6, a plurality of lower leashes 34 may be implemented, connecting at secondary ring 36 located on the leash system 20.

As illustrated in FIGS. 1 and 6, safety hook 22B at the far-end of the lower leash 34 can attach to an animal harness or collar 100. In this embodiment, lower leash 34 connects from secondary ring 36, connecting upper leash 32 to lower leash 34 and further connecting to an animal collar or harness 100. As depicted in FIGS. 5-6, lower leash 34 that connects to the animal collar or harness 100 can be an elastic cord with durable elasticity with fabric calling longer than the elastic cord, bunched to allow for extension of the elastic cord. There may further be a strap or feature (not shown) on the lower-end of lower leash 34 that controls overstretching or breaking of lower leash 34. It will be appreciated that this feature may also be included in upper leash 32 and/or the entire leash 24. The elastic nature of lower leash 34, upper leash 32, and/or leash 24 reduces the physical impact on the user of the human support device 50 as well as reduces the physical impact on the animal attached to the leash system 20. This feature allows for a more comfortable and enjoyable walking experience for both animal and human. It will be appreciated that upper leash 32 and/or lower leash 34 may be made from a variety of materials including, but not limited to, an elastic cord, nylon, leather, or metal chain.

By coupling the human support device 50 and leash system 20, the user receives the benefits of a hands-free animal walking system that also focuses on improving the health and safety of the user that no other system provides. By securing the back, neck, and shoulders of the user, the user can walk longer and safer. The system 10 improves the experience for users with physical limitations or users of an advanced age. This is achieved through the ergonomic structural support provided by the human support device 50 used in tandem with animal leash system 20, as the force from the animal is distributed evenly by the human support device 50.

As illustrated in FIGS. 5-6, the system 10 may also include at least one graspable handle 110 for measuring health metrics. By applying the hands-free availability from the at least one pocket 70(a), (b), and (c) of the human support device 50, at least one of handles 110 may utilize digital sensors for measuring health metrics. The handle(s) 110 may be coupled to primary ring 68 on the belt 64 through use of a cord 112, rope, or similar connecting apparatus. It will be further appreciated that the handles 110 may attach to secondary ring 36 located on animal leash system 20, as illustrated in FIGS. 5-6. It will be appreciated that handle(s) 110 may attach at multiple points of the system 10 utilizing a variety of fastening methods including, but not limited to safety hooks, magnets, clamps, or bolts. In an exemplary embodiment, the system 10 could also utilize digital, BLUETOOTH®, or otherwise cordless handles and digital sensors.

The digital sensors located on handle(s) 110 may be used to track health metrics such as pulse, oxygen levels, steps, elevation, and other metrics. The digital sensors may also sync with applications on the user's phone or computer using a physical cord connection from the handles to the phone or computer, or the handles may connect through a wireless method such as Bluetooth. In addition to health measuring metrics, the application may include features that collet data and information to provide the user with goal setting features such as time goals, calorie goals, or step goals. Further, the application could also contain a warning system for the user, warning the user of health risks such as high blood pressure, high heart rate, etc. The more users utilizing this feature only enhances the benefits of the health monitoring, particularly when the users live in close proximity to one another. By comparing and even competing against neighbors and friends motivates users to walk more often and longer. This bolsters the community spirit and improves the well-being of the individuals in the community.

Depending on the embodiment, the digital sensors may be located in other locations of the present invention. Digital sensors may be located on the vest 52, the human support device 50, graspable handle(s) 110, shoes, and/or as wearable patches. It will be appreciated that there are multiple methods of securing digital sensors to the present invention including, but not limited to, magnets, sewing digital sensors in the fabric, clamps, or other fastening methods.

In one embodiment of the present invention 10 as shown in FIGS. 3-4, the human support device 50 may also contain at least one pocket for storing the animal leash system 20, handles 110, and other parts of the present invention. As illustrated in FIG. 5, back pocket 70(c) can function as this storage method. It will be appreciated that the location, size, and type of pocket may vary based on the embodiment. Further, the pocket in this embodiment is closed using a zipper, but depending on the embodiment the method of fastening may vary. Other methods of securing the storage pocket include, but is not limited to, a flap, buttonhole, or notch fastener.

From the foregoing, it will be seen that this invention is one well adapted to attain all the ends and objects hereinabove set forth together with other advantages which are obvious and which are inherent to the structure. It will be understood that certain features and sub combinations are of utility and may be employed without reference to other features and sub combinations. This is contemplated by and is within the scope of the claims. Since many possible embodiments of the invention may be made without departing from the scope thereof, it is also to be understood that all matters herein set forth or shown in the accompanying drawings are to be interpreted as illustrative and not limiting.

The constructions described above and illustrated in the drawings are presented by way of example only and are not intended to limit the concepts and principles of the present invention. Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. The terms "having" and "including" and similar terms as used in the foregoing specification are used in the sense of "optional" or "may include" and not as "required." Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. A animal harness and leash system comprising:
    a human support device further including: (a) a back center support strap, (b) two shoulder straps; (c) an adjustable body strap, and (d) a vest, said vest at least partially encasing said human support device; and
    an animal leash system with said animal leash system coupled to said human support device;
    wherein said two shoulder straps are coupled by a buckle.

2. The system of claim 1, wherein said human support device further includes at least one sternum strap, at least one sternum strap fastener, and at least one sternum strap adjuster.

3. The system of claim 1, wherein said adjustable body strap includes a primary ring with hardware to attach said leash system to said body strap.

4. The system of claim 3, wherein said human support device includes at least one storage pocket, wherein said at least one storage pocket is located on said vest.

5. The system of claim 1, wherein said animal leash system consists of an elastic cord.

6. The system of claim 5, wherein said animal leash system includes at least one fastener for coupling said animal leash system to said human support device.

7. A animal harness and leash system comprising:
    a human support device further including: (a) a back center support strap, (b) at least one shoulder strap; and (c) an adjustable body strap; and
    an animal leash system with said animal leash system coupled to said human support device;
    wherein said human support device includes at least one graspable handle, said at least one graspable handle is coupled to said human support device;
    wherein said graspable handles includes at least one digital sensor for collecting health metrics from the user.

* * * * *